(12) United States Patent
Yao et al.

(10) Patent No.: US 12,128,082 B2
(45) Date of Patent: Oct. 29, 2024

(54) **METHOD FOR EXTRACTING FLAVONE AGLYCONES IN *CHRYSANTHEMUM MORIFOLIUM*, EXTRACT OBTAINED THEREBY AND ANTI-INFLAMMATORY PHARMACEUTICAL COMPOSITION**

(71) Applicant: INDUSTRIAL TECHNOLOGY RESEARCH INSTITUTE, Hsinchu (TW)

(72) Inventors: Hsin Jan Yao, Taixi Township (TW); Yu-Wen Chen, Zhubei (TW); Chu-Hsun Lu, Hsinchu (TW); I-Hong Pan, Zhubei (TW); Wen-Yin Chen, Tainan (TW); Tsung-Lin Yang, Tainan (TW); Angela Goh, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 128 days.

(21) Appl. No.: 17/560,487

(22) Filed: Dec. 23, 2021

(65) Prior Publication Data

US 2023/0201291 A1 Jun. 29, 2023

(51) Int. Cl.
*A61K 36/287* (2006.01)
*A61P 29/00* (2006.01)

(52) U.S. Cl.
CPC ............ *A61K 36/287* (2013.01); *A61P 29/00* (2018.01); *A61K 2236/31* (2013.01); *A61K 2236/331* (2013.01); *A61K 2236/333* (2013.01); *A61K 2236/53* (2013.01); *A61K 2236/55* (2013.01)

(58) Field of Classification Search
None
See application file for complete search history.

(56) References Cited

U.S. PATENT DOCUMENTS

| | | | |
|---|---|---|---|
| 8,624,084 B2 | 1/2014 | Coruzzi et al. | |
| 10,967,031 B2 | 4/2021 | Rozenblat et al. | |
| 10,987,394 B2 | 4/2021 | Pan et al. | |
| 11,064,658 B2 | 7/2021 | Chen et al. | |

FOREIGN PATENT DOCUMENTS

| | | | |
|---|---|---|---|
| CN | 1590397 A | | 3/2005 |
| CN | 101248870 A | * | 8/2008 |
| CN | 101955688 A | | 1/2011 |
| CN | 101991090 A | | 3/2011 |
| CN | 102228498 A | | 11/2011 |
| CN | 103479704 A | | 1/2014 |
| CN | 103689158 A | | 4/2014 |
| CN | 103933096 A | | 7/2014 |
| CN | 103478840 B | | 6/2015 |
| CN | 104840501 A | | 8/2015 |
| CN | 109078034 A | | 12/2018 |
| CN | 109221269 A | | 1/2019 |
| CN | 110123859 A | | 8/2019 |
| CN | 110754596 A | | 2/2020 |
| CN | 105267275 B | | 4/2020 |
| CN | 111983095 A | | 11/2020 |
| CN | 112341418 A | | 2/2021 |
| FR | 2 732 593 B1 | | 5/1997 |
| JP | 2015-212236 A | | 11/2015 |
| JP | 2019-115318 A | | 7/2019 |
| KR | 20090106700 A | * | 10/2009 |
| KR | 10-2011-0131822 A | | 12/2011 |
| KR | 10-2016-0005162 A | | 1/2016 |
| KR | 10-1738075 B1 | | 5/2017 |
| KR | 10-2019-0088383 A | | 7/2019 |
| TW | I684456 B | | 2/2020 |
| TW | 202037377 A | | 10/2020 |
| WO | WO 2018/174502 A1 | | 9/2018 |
| WO | 2019/070056 A1 | | 11/2019 |
| WO | WO 2021/084132 A1 | | 4/2021 |

OTHER PUBLICATIONS

Ahn Jarvis et al., "Modulating conversion of isoflavone glycosides to aglycones using crude beta-glycosidase extracts from almonds and processed soy," Food Chemistry, vol. 237, 2017, pp. 685-692, 8 pages total.
De Lima et al., "The effects of soybean soaking on grain properties and isoflavones loss," LWT—Food Science and Technology, vol. 59, 2014, pp. 1274-1282, 9 pages total.
Góes-Favoni et al., "Changes of isoflavone in soybean cotyledons soaked in different volumes of water," Food Chemistry, vol. 119, 2010, pp. 1605-1612, 8 pages total.
Han et al., "Phytochemical Composition and Antioxidant Activities of Two Different Color Chrysanthemum Flower Teas," Molecules, vol. 24, No. 329, 2019, pp. 1-14, 14 pages total.
He et al., "Total flavonoids of Flos Chrysanthemi protect arterial endothelial cells against oxidative stress," Journal of Ethnopharmacology, vol. 139, 2012, pp. 68-73, 6 pages total.
Hostetler et al., "Effects of food formulation and thermal processing on flavones in celery and chamomile," Food Chemistry, vol. 141, No. 2, 2013, pp. 1-14, 14 pages total.
Hostetler et al., "Endogenous Enzymes, Heat, and pH Affect Flavone Profiles in Parsley (*Petroselinum crispum var. neapolitanum*) and Celery (*Apium graveolens*) during Juice Processing," Journal of Agricultural and Food Chemistry, vol. 60, No. 1, 2012, pp. 1-19.
Hostetler et al., "Flavone deglycosylation increases their anti-inflammatory activity and absorption," Molecular Nutrition & Food Research, vol. 56, 2012, pp. 558-569, 12 pages total.

(Continued)

*Primary Examiner* — Susan Hoffman
(74) *Attorney, Agent, or Firm* — Birch, Stewart, Kolasch & Birch, LLP

(57) ABSTRACT

A method for extracting flavone aglycones in *Chrysanthemum morifolium* is provided. The method includes: (a) immersing a *Chrysanthemum morifolium* raw material in water or an aqueous solution to perform an immersion procedure for 3.5 hours or more to obtain an immersion sample; and (b) adding an extraction solvent to the immersion sample to perform an extraction procedure 5-60 minutes to obtain an extract. The *Chrysanthemum morifolium* raw material includes at least one of the following parts of *Chrysanthemum morifolium*: whole plant, roots, stems, leaves and flowers.

18 Claims, 8 Drawing Sheets

(56) References Cited

OTHER PUBLICATIONS

Lee et al., "A new anti-HIV flavonoid glucuronide from *Chrysanthemum morifolium*", Planta Medica, 2003, 1 page total.

Li et al., "Chemical compositions of chrysanthemum teas and their anti-inflammatory and antioxidant properties," Food Chemistry, vol. 286, 2019, pp. 8-16, 9 pages total.

Liu et al., "Extraction of flavonoids from *Chrysanthemum morifolium* and antitumor activity in vitro," Experimental and Therapeutic Medicine, vol. 15, 2018, pp. 1203-1210, 8 pages total.

Pei et al., "Effect of chrysanthemum extract on myocardial fibrosis in rats with renovascular hypertension," Journal of Traditional Chinese Medicine, vol. 39, No. 4, 2019, pp. 542-549, 8 pages total.

Ryu et al., "Chrysanthemum Leaf Ethanol Extract Prevents Obesity and Metabolic Disease in Diet-Induced Obese Mice via Lipid Mobilization in White Adipose Tissue," Nutrients, vol. 11, No. 1347, 2019, pp. 1-16, 16 pages total.

Ukiya et al., "Constituents of Compositae Plants. 2. Triterpene Diols, Triols, and Their 3-O-Fatty Acid Esters from Edible Chrysanthemum Flower Extract and Their Anti-inflammatory Effects," Journal of Agricultural and Food Chemistry, vol. 49, 2001, pp. 3187-3197, 11 pages total.

Wang et al., "Antioxidant activities of aqueous extracts from 12 Chinese edible flowers in vitro and in vivo," Food & Nutrition Research, vol. 61, No. 1, 2016, pp. 1-9, 9 pages total.

Xie et al., "Cytotoxic activity of flavonoids from the flowers of *Chrysanthemum morifolium* on human colon cancer Colon205 cells," Journal of Asian Natural Products Research, vol. 11, No. 9, 2009, 4 pages total.

Xue et al., "Characterization of Composition and Antifungal Properties of Leaf Secondary Metabolites from Thirteen Cultivars of *Chrysanthemum morifolium* Ramat.," Molecules, vol. 24, No. 4202, 2019, pp. 1-11, 11 pages total.

Yan et al., "Influence of Enzyme Hydrolysis on Flavonoid Aglycones in Total Flavonoids in Chrysanthemum morifolium Ramat," Anhui University of Chinese Medicine, 2016, 4 pages total, with an English abstract.

Yang et al., "Neuroprotective Caffeoylquinic Acid Derivatives from the Flowers of *Chrysanthemum morifolium*," Journal of Natural Products, vol. 80, No. 4, 2017, pp. 1028-1033, 6 pages total.

Taiwanese Office Action and Search Report for Taiwanese Application No. 110148329, dated Aug. 17, 2022.

Wu et al., "Anti-inflammatory effect and mechanism study of total flavonoids in Chrysanthemum morif olium Ramat," Chinese Journal of Clinical Pharmacology and Therapeutics, 2009, 5 pages total, with an English abstract.

Yin et al., "Study on extraction technology for extract and flavonoids in *Chrysanthemum morifolium* by orthogonal design," China Journal of Chinese Materia Medica, vol. 29, 2004, 3 pages total, with an English abstract.

Extended European Search Report for European Application No. 21217409.8, dated May 20, 2022.

Lii et al., "Chrysanthemum morifolium Ramat. reduces the oxidized LDL-induced expression of intercellular adhesion molecule-1 and E-selectin in human umbilical vein endothelial cells" Journal of Ethnopharmacology, vol. 128, No. 1, Mar. 2, 2010, pp. 213-220, 8 pages total.

"Inhibiting slight inflammation on epidermis and then inhibiting melanin production_ High penetration with unique technology-Low molecular weight purple chrysanthemum luteolin", Feb. 26, 2019, with english translation.

"Raw material derived from edible yellow chrysanthemum is wrinkle/spot care: High penetration with unique technology-Low molecular weight yellow chrysanthemum apigenin", Jan. 31, 2019, with english translation.

Chinese Office Action and Search Report for Chinese Application No. 202111588334.1, dated Jan. 5, 2024.

Japanese Office Action for Japanese Application No. 2021-209197, dated Dec. 1, 2023.

Li et al., "An efficient method for the simultaneous determination of three flavone aglycones in Flos Chrysanthemi by acid hydrolysis and HPLC", Journal of Chinese Pharmaceutical Sciences, vol. 18, 2009, pp. 55-60.

Liu et al., "Preparation, Identification and Purification of Apigenin", Modern Food Science and Technology, vol. 29, No. 12, 2013, pp. 2947-2952, with partial translation.

* cited by examiner

METHOD FOR EXTRACTING FLAVONE AGLYCONES IN *CHRYSANTHEMUM MORIFOLIUM*, EXTRACT OBTAINED THEREBY AND ANTI-INFLAMMATORY PHARMACEUTICAL COMPOSITION

TECHNICAL FIELD

The present disclosure relates to a method for extracting flavone aglycones in *Chrysanthemum morifolium*, an extract obtained thereby and an anti-inflammatory pharmaceutical composition.

BACKGROUND

*Chrysanthemum morifolium* belongs to the Asteraceae family of plants. It is a perennial herb, mainly produced in regions of Asia such as Taiwan and China.

The capitulum of *Chrysanthemum morifolium* can be used as a drink after drying, and it is also a traditional medicinal plant. Modern pharmacological studies have shown that *Chrysanthemum morifolium* has antioxidant, anti-inflammatory, antiviral, antitumor, neuroprotective and cardiovascular protective effects. *Chrysanthemum morifolium* contains chrysanthemin, amino acids, flavonoids and various vitamins and trace elements. The chemical composition of *Chrysanthemum morifolium* is complex, among which flavonoids, triterpenoids and volatile oils are its main active ingredients, however, due to differences in origin and variety, the chemical compositions and contents of *Chrysanthemum morifolium* from different sources are different.

Flavonoids are a secondary metabolite synthesized by plants, and they play an important role in plant growth, development, flowering, fruiting, and antibacterial and disease prevention. Flavonoids are usually combined with sugars in plants to form glycosides while a small part exists in the form of free state (aglycones). Previous studies have shown that free glycogen flavonoids have better anti-inflammatory activity than glycoside derivatives. In recent years, many researchers have tried to hydrolyze flavonoid glycoside derivatives into free glycosides using enzymatic hydrolysis or microbial fermentation, however, additional enzymes or microbial fermentation have greatly increased the extraction cost.

Therefore, at present, there is a need for a novel flavonoid aglycone extraction method, which can effectively extract the flavonoid aglycones of *Chrysanthemum morifolium*, but does not require any addition of enzymes and/or microbial treatment.

SUMMARY

The present disclosure provides a method for extracting flavone aglycones in *Chrysanthemum morifolium*, comprising: (a) immersing a *Chrysanthemum morifolium* raw material in water or an aqueous solution to perform an immersion procedure for 3.5 hours or more to obtain an immersion sample; and (b) adding an extraction solvent to the immersion sample to perform an extraction procedure for 5-60 minutes to obtain an extract solution. The *Chrysanthemum morifolium* raw material comprises at least one of the following parts of a *Chrysanthemum morifolium*: a whole plant, a root, a stem, a leaf and a flower, a weight ratio of the *Chrysanthemum morifolium* raw material to the water or the aqueous solution is 1:10-35, the immersion procedure is performed at 20 to 70° C., the water or the aqueous solution has a pH value of 3.0 to 9.5, and the immersion sample comprises an immersed *Chrysanthemum morifolium* raw material and an immersion solution. Moreover, a weight ratio of the *Chrysanthemum morifolium* raw material to the extraction solvent is 1:10-35, the extraction solvent comprises methanol, ethanol or ethyl acetate, the extraction procedure is performed at 15 to 50° C., and the extract solution contains flavone aglycones.

The present disclosure also provides a *Chrysanthemum morifolium* extract, which is obtained by the method for extracting flavone aglycones in *Chrysanthemum morifolium* mentioned above.

The present disclosure also provides an anti-inflammatory pharmaceutical composition, comprising: a *Chrysanthemum morifolium* extract obtained by the method for extracting flavone aglycones in *Chrysanthemum morifolium* mentioned above; and a pharmaceutically acceptable carrier or salt.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1:
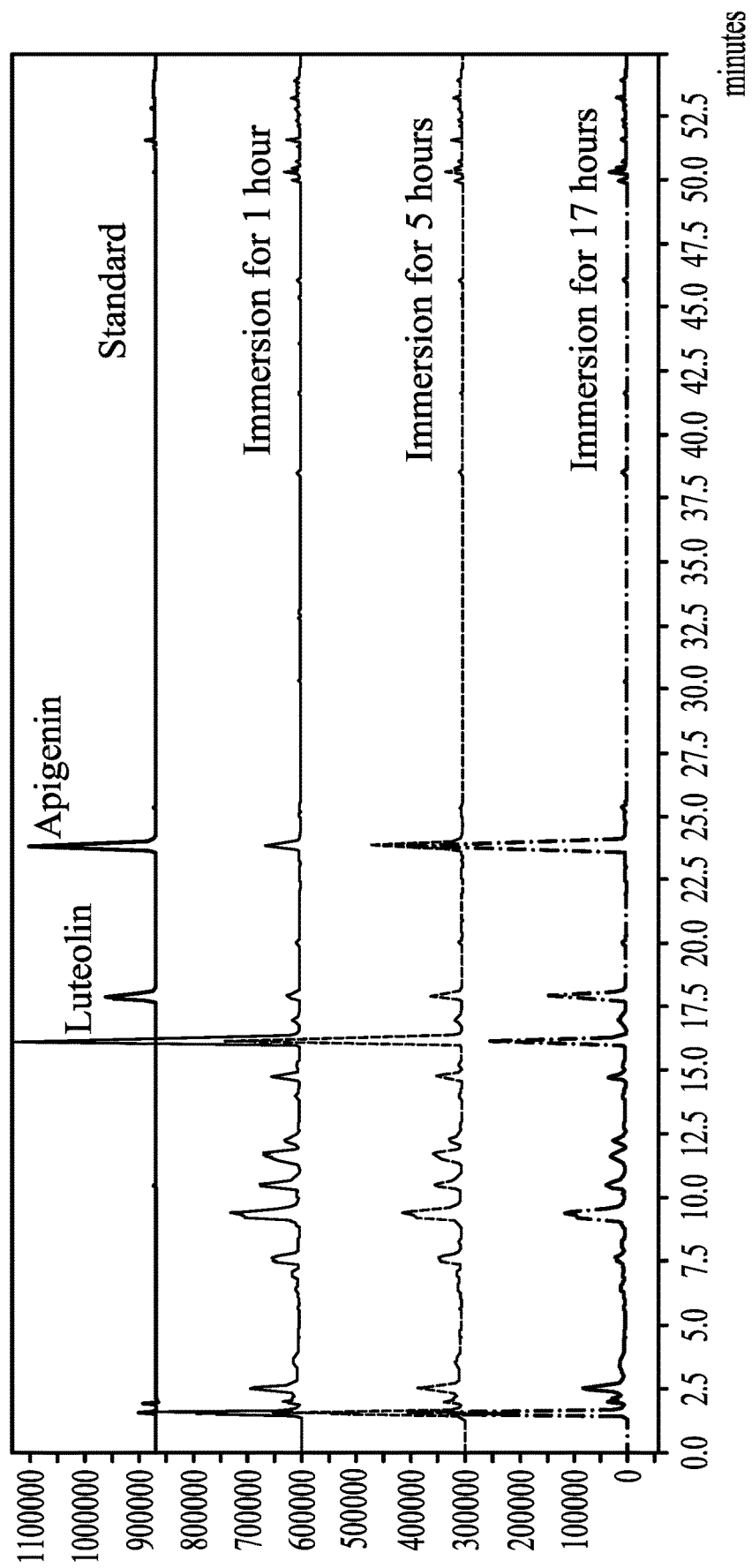
FIG. 1 shows the high performance liquid chromatograms of the extract solutions of the flowers of *Chrysanthemum morifolium* with different immersion time.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a method for extracting flavone aglycones in *Chrysanthemum morifolium*. Moreover, the flavone aglycones mentioned above may comprise, but is not limited to, luteolin, apigenin, etc., or combinations thereof.

The method for extracting flavone aglycones in *Chrysanthemum morifolium* of the present disclosure can effectively extract the flavonoid aglycones in *Chrysanthemum* only through a water or aqueous solution immersion step, without additional addition of any enzyme. Furthermore, even if the method for extracting flavone aglycones in *Chrysanthemum morifolium* of the present disclosure is performed at room temperature for whole process, the flavonoid aglycones in the *Chrysanthemum morifolium* can still be effectively extracted. Therefore, the method for extracting flavone aglycones in *Chrysanthemum morifolium* of the present disclosure can effectively reduce the extraction cost, and has the effect of energy saving and carbon reduction.

In addition, by using the method for extracting flavone aglycones in *Chrysanthemum morifolium* of the present disclosure, the extraction rate of flavonoid aglycones in the *Chrysanthemum morifolium* raw material can be greatly increased.

Moreover, the method for extracting flavone aglycones in *Chrysanthemum morifolium* of the present disclosure mentioned above may comprise, but is not limited to the following steps.

First, a *Chrysanthemum morifolium* raw material is immersed in water or an aqueous solution to perform an immersion procedure for 3.5 hours or more to obtain an immersion sample. Furthermore, the immersion sample may comprise an immersed *Chrysanthemum morifolium* raw material and an immersion solution.

Moreover, in the method for extracting flavone aglycones in *Chrysanthemum morifolium* of the present disclosure, the *Chrysanthemum morifolium* raw material mentioned above may comprise at least one of the following parts of a *Chrysanthemum morifolium*: a whole plant, a root, a stem, a leaf and a flower. In one embodiment, the *Chrysanthemum morifolium* raw material mentioned above may be a flower of the *Chrysanthemum morifolium*. In another embodiment, the *Chrysanthemum morifolium* raw material mentioned above may be a stem or a leaf of the *Chrysanthemum morifolium*.

In one embodiment, the *Chrysanthemum morifolium* raw material mentioned above may be subjected to a pretreatment. The pretreatment mentioned above comprises a drying treatment, a pulverizing treatment, etc., or any combinations thereof. In one embodiment, the pretreatment mentioned above comprises a drying treatment and a pulverizing treatment.

Furthermore, in the method for extracting flavone aglycones in *Chrysanthemum morifolium* of the present disclosure, except that it has to be 3.5 hours or more, the time for performing the immersion procedure mentioned above has no particular limitation and can depend on the operating environment at the time (such as temperature, humidity, pressure, etc.), the weight of *Chrysanthemum morifolium* raw material, the state of *Chrysanthemum morifolium* raw material (such as the degree of pulverization, water content) and/or the immersion temperature to be used, etc. For example, the time for performing the immersion procedure mentioned above may be about 3.5 to 96 hours, about 4 to 96 hours, about 5 to 96 hours, about 5 to 72 hours, about 3.5 hours, about 4 hours, about 5 hours, about 6 hours, about 10 hours, about 12 hours, about 15 hours, about 16 hours, about 17 hours, about 18 hours, about 20 hours, about 21 hours, about 24 hours, about 27 hours, about 30 hours, about 36 hours, about 40 hours, about 48 hours, about 60 hours, about 72 hours, about 96 hour, but it is not limited thereto. In one embodiment, in the method for extracting flavone aglycones in *Chrysanthemum morifolium* of the present disclosure, the immersion procedure mentioned above is performed for about 5, 17 or 24 hours. In another embodiment, in the method for extracting flavone aglycones in *Chrysanthemum morifolium* of the present disclosure, the immersion procedure mentioned above is performed for about 5, 24, 48 or 72 hours.

Moreover, in the method for extracting flavone aglycones in *Chrysanthemum morifolium* of the present disclosure, the temperature for performing the immersion procedure mentioned above may be about 20° C. to 70° C., about 20° C. to 65° C., about 25° C. to 70° C. or room temperature to about 70° C., about 25° C. to 60° C. or room temperature to about 60° C., about 25° C. to 50° C. or room temperature to about 50° C., about 25° C. to 40° C. or room temperature to about 40° C., about 20° C., about 25° C., room temperature, about 40° C., about 50° C., about 55° C., about 60° C., about 65° C., about 70° C., but it is not limited thereto. In one embodiment, in the method for extracting flavone aglycones in *Chrysanthemum morifolium* of the present disclosure, the immersion procedure mentioned above is performed at room temperature. In another embodiment, in the method for extracting flavone aglycones in *Chrysanthemum morifolium* of the present disclosure, the immersion procedure mentioned above is performed at about 50° C.

In addition, in the method for extracting flavone aglycones in *Chrysanthemum morifolium* of the present disclosure, a weight ratio of the foregoing *Chrysanthemum morifolium* raw material to the foregoing water or aqueous solution has no particular limitation, as long as the foregoing water or aqueous solution can cover the foregoing *Chrysanthemum morifolium* raw material, so that the foregoing *Chrysanthemum morifolium* raw material can be immersed therein. In one embodiment, the weight ratio of the foregoing *Chrysanthemum morifolium* raw material to the foregoing water or aqueous solution may be about 1:10-35, such as about 1:15-30, about 1:15-20, about 1:10, about 1:15, about 1:20, about 1:25, about 1:30, but it is not limited thereto. In one specific embodiment, the weight ratio of the foregoing *Chrysanthemum morifolium* raw material to the foregoing water or aqueous solution may be about 1:20.

In the method for extracting flavone aglycones in *Chrysanthemum morifolium* of the present disclosure, the foregoing water or aqueous solution has a pH value of about 3.0 to 9.5, such as a pH value of about 4.0 to 9.5, a pH value of about 5.0 to 9.2, a pH value of about 3.0, a pH value of about 4.0, a pH value of about 5.0, a pH value of about 7, a pH value of about 7.18, a pH value of about 9, a pH value of about 9.2, a pH value of about 9.5, but it is not limited thereto.

Next, in the method for extracting flavone aglycones in *Chrysanthemum morifolium* of the present disclosure, after a *Chrysanthemum morifolium* raw material is immersed in water or an aqueous solution to perform an immersion procedure for 3.5 hours or more to obtain an immersion sample, an extraction solvent is added to the immersion sample to perform an extraction procedure to obtain an extract solution. The extract solution mentioned above contains flavone aglycones.

The extraction solvent mentioned above has no particular limitation, as long as it can dissolve the flavonoid aglycone in the immersion sample or the immersed *Chrysanthemum morifolium* raw material mentioned above, and has no adverse effect thereon. Examples of the extraction solvent mentioned above may comprise, but are not limited to, methanol, ethanol, ethyl acetate or any combinations thereof. A concentration of the ethanol mentioned above may be about 50-95%, but it is not limited thereto. In one embodiment, the extraction solvent mentioned above is ethanol.

In the method for extracting flavone aglycones in *Chrysanthemum morifolium* of the present disclosure, the time for performing the extraction procedure mentioned above has no particular limitation and can depend on the operating environment at the time (such as temperature, humidity, pressure, etc.), a volume and/or a weight of the immersion sample or the immersed *Chrysanthemum morifolium* raw material and/or the extraction temperature to be used, etc. For example, the time for performing the extraction procedure mentioned above may be about 5 to 60 minutes, about 10 to 60 minutes, about 10 to 55 minutes, about 10 to 45 minutes, about 10 to 40 minutes, about 15 to 30 minutes, about 10 minutes, about 15 minutes, about 20 minutes, about 25 minutes, about 30 minutes, about 35 minutes, about 40 hours, about 45 hours, about 50 hours, about 55 hours, about 60 hours, but it is not limited thereto. In one embodiment, in the method for extracting flavone aglycones in *Chrysanthemum morifolium* of the present disclosure, the extraction procedure mentioned above is performed for about 30 minutes.

Furthermore, in the method for extracting flavone aglycones in *Chrysanthemum morifolium* of the present disclosure, the temperature for performing the extraction procedure mentioned above may be about 15° C. to 50° C., about 15° C. to 45° C., about 20° C. to 40° C., about 25° C. to 40° C. or room temperature to about 40° C., about 15° C., about 20° C., about 25° C., a room temperature, about 30° C., about 35° C., about 40° C., about 45° C., about 50° C., but it is not limited thereto. In one embodiment, in the method for extracting flavone aglycones in *Chrysanthemum morifolium* of the present disclosure, the extraction procedure mentioned above is performed at room temperature.

In the method for extracting flavone aglycones in *Chrysanthemum morifolium* of the present disclosure, a weight ratio of the foregoing *Chrysanthemum morifolium* raw material to the foregoing extraction solvent has no particular limitation. In one embodiment, the weight ratio of the foregoing *Chrysanthemum morifolium* raw material to the foregoing extraction solvent may be about 1:10-35, such as about 1:15-30, about 1:15-20, about 1:10, about 1:15, about 1:20, about 1:25, about 1:30, but it is not limited thereto. In one specific embodiment, the weight ratio of the foregoing *Chrysanthemum morifolium* raw material to the foregoing extraction solvent may be about 1:20.

In one embodiment, the method for extracting flavone aglycones in *Chrysanthemum morifolium* of the present disclosure, the extraction procedure mentioned above may be performed under shaking or stirring, but it is not limited thereto. The shaking mentioned above may comprise, but is not limited to, ultrasonic oscillation, rotary oscillation, etc. Moreover, the manner for the stirring mentioned above may be performing the stirring by a stirrer, such as a paddle agitator, an electromagnetic stirrer, but it is also not limited thereto.

In addition, in one embodiment, the method for extracting flavone aglycones in *Chrysanthemum morifolium* of the present disclosure, further comprises between the step of immersing a *Chrysanthemum morifolium* raw material in water or an aqueous solution to perform an immersion procedure for 3.5 hours or more to obtain an immersion sample and the step of adding an extraction solvent to the immersion sample to perform an extraction procedure to obtain an extract solution, removing the immersion solution mentioned above in the immersion sample mentioned above. Namely, the extraction solvent only reacts with the immersed *Chrysanthemum morifolium* raw material mentioned above.

Moreover, in one embodiment, the method for extracting flavone aglycones in *Chrysanthemum morifolium* of the present disclosure may further comprise after the step of adding an extraction solvent to the immersion sample to perform an extraction procedure to obtain an extract solution, performing a solid-liquid separation procedure on the extract solution to obtain a supernatant, while the supernatant contains the flavone aglycones mentioned above.

The solid-liquid separation procedure has no particular limitation, as long as it can separate the solid from the liquid in the extract solution. Examples of the solid-liquid separation procedure may comprise, but is not limited to centrifugation or filtration.

Furthermore, in one specific embodiment, the method for extracting flavone aglycones in *Chrysanthemum morifolium* of the present disclosure may further comprise after obtaining the supernatant mentioned above, further separating and purifying the flavonoid aglycones mentioned above from the supernatant mentioned above.

Alternatively, in another specific embodiment, the method for extracting flavone aglycones in *Chrysanthemum morifolium* of the present disclosure may further comprise after obtaining the supernatant mentioned above, further performing a concentration procedure to obtain a concentrated solution while the concentrated solution mentioned above contains the flavone aglycones mentioned above. Moreover, in this specific embodiment, the method for extracting flavone aglycones in *Chrysanthemum morifolium* of the present disclosure also may further comprise after obtaining the concentrated solution mentioned above, further separating and purifying the flavonoid aglycones mentioned above from the concentrated solution mentioned above.

In one specific embodiment, in the method for extracting flavone aglycones in *Chrysanthemum morifolium* of the present disclosure, the *Chrysanthemum morifolium* raw material mentioned above is a flower of the *Chrysanthemum morifolium*. Furthermore, in this specific embodiment, the immersion procedure mentioned above is performed for 5 to 72 hours, the weight ratio of the *Chrysanthemum morifolium* raw material mentioned above to the water or the aqueous solution is 1:15-20, the immersion procedure mentioned above is performed at room temperature to 50° C., the water or the aqueous solution mentioned above has a pH value of 5.0 to 9.2, and the extraction solvent mentioned above is ethanol. Moreover, in this specific embodiment, an extraction rate of flavone aglycones of the *Chrysanthemum morifolium* raw material in the method for extracting flavone aglycones in *Chrysanthemum morifolium* of the present disclosure may be 2-30 mg flavone aglycones/g *Chrysanthemum morifolium* raw material.

In another specific embodiment, in the method for extracting flavone aglycones in *Chrysanthemum morifolium* of the present disclosure, the *Chrysanthemum morifolium* raw material mentioned above is a stem and a leaf of the *Chrysanthemum morifolium*. Furthermore, in this specific embodiment, the immersion procedure mentioned above is performed for 5 to 72 hours, the weight ratio of the *Chrysanthemum morifolium* raw material mentioned above to the water or the aqueous solution is 1:15-20, the immersion procedure mentioned above is performed at room temperature to 50° C., the water or the aqueous solution mentioned above has a pH value of 5.0 to 9.2, and the extraction solvent mentioned above is ethanol. Moreover, in this specific embodiment, an extraction rate of flavone aglycones of the *Chrysanthemum morifolium* raw material in the method for extracting flavone aglycones in *Chrysanthemum morifolium* of the present disclosure may be 2-25 mg flavone aglycones/g *Chrysanthemum morifolium* raw material.

Based on the foregoing, the present disclosure may further provide a *Chrysanthemum morifolium* extract, which may be obtained by any method for extracting flavone aglycones in *Chrysanthemum morifolium* of the present disclosure mentioned above.

Moreover, the *Chrysanthemum morifolium* extract of the present disclosure mentioned above has an excellent anti-inflammatory effect.

Therefore, the present disclosure also provide an anti-inflammatory pharmaceutical composition which may comprise, but is not limited to, a *Chrysanthemum morifolium* extract obtained by any method for extracting flavone aglycones in *Chrysanthemum morifolium* of the present disclosure mentioned above.

The present disclosure mentioned above also provides an anti-inflammatory pharmaceutical composition which may further comprise a pharmaceutically acceptable carrier or salt, but it is not limited thereto.

The pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Moreover, the pharmaceutically acceptable salt mentioned above may comprise, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

Furthermore, the pharmaceutical composition of the present disclosure can be administered to a subject in need thereof, but is not limited thereto. The administration route of the pharmaceutical composition of the present disclosure may include parenteral manner, oral manner, via inhalation spray, or by implanted reservoir, but is not limited thereto. The parenteral methods may comprise, but is not limited to, smearing affected region, subcutaneous, intracutaneous, intravenous, intramuscular, intra-articular, intra-arterial, intrasynovial, intrasternal, intrathecal, intralesional injection, external ophthalmic use, and intraocular injection, as well as infusion techniques, etc.

Topical use form for smearing may include ointment, emulsion, liquid, gel, etc., but it is not limited thereto.

In addition, the subject in need to be administrated the pharmaceutical composition mentioned above may comprise, but is not limited to, a vertebrate. Moreover, the vertebrate mentioned above may comprise a fish, an amphibian, a reptile, a bird or a mammal, but it is not limited thereto. Examples of the mammal may comprise, but are not limited to a human, an orangutan, a monkey, a horse, a donkey, a dog, a cat, a rabbit, a guinea pig, a rat and a mouse. In one embodiment, the subject mentioned above may be a human.

EXAMPLES

A. Material

A-1. Pretreatment for *Chrysanthemum morifolium* Raw Material

A-1-1. Pretreatment for Flowers of *Chrysanthemum morifolium*

After flowers of *Chrysanthemum morifolium* were harvested, they were placed at room temperature for wilting for 2 hours (the time should not exceed 6 hours) to make them lose water evenly.

Next, the flowers of *Chrysanthemum morifolium* were subjected to a drying procedure to make the moisture content thereof was less than 10%. The drying procedure mentioned above could be drying at 50° C. for 4-8 hours, drying at 60° C. for 4-8 hours, or drying at 70° C. for 2-4 hours. After that, the dried flowers of *Chrysanthemum morifolium* mentioned above were pulverized by a pulverizer to obtain dried crumble of the flowers of *Chrysanthemum morifolium*.

A-1-2. Pretreatment for Stems and Leaves of *Chrysanthemum morifolium*

After stems and leaves of *Chrysanthemum morifolium* were harvested, without a wilting procedure, they were dried at 45° C. for 48 hours to make the moisture content thereof was less than 10%.

After that, the dried stems and leaves of *Chrysanthemum morifolium* mentioned above were pulverized by a pulverizer to obtain dried crumble of the stems and leaves of *Chrysanthemum morifolium*.

A-2. Preparation of Buffers with Different pH Values

A-2-1. Preparation of pH 2.7, pH 5.0 and pH 7.18 Citrate-Phosphate Buffers 0.1 M citric acid (2.1 g dissolved in 100 mL water) stock solution and 0.2 M $Na_2HPO_4$ (2.84 g dissolved in 100 mL water) stock solution were prepared, respectively.

(1) Preparation of pH 2.7 Citrate-Phosphate Buffer 89.1 mL of the 0.1 M citric acid stock solution mentioned above was mixed with 10.9 mL of the 0.2 M $Na_2HPO_4$ stock solution mentioned above to obtain a pH 2.7 citrate-phosphate buffer.

(2) Preparation of pH 5.0 Citrate-Phosphate Buffer 53.25 mL of the 0.1 M citric acid stock solution mentioned above was mixed with 46.75 mL of the 0.2 M $Na_2HPO_4$ stock solution mentioned above to obtain a pH 5.0 citrate-phosphate buffer.

(3) Preparation of pH 7.18 Citrate-Phosphate Buffer 17.65 mL of the 0.1 M citric acid stock solution mentioned above was mixed with 82.35 mL of the 0.2 M $Na_2HPO_4$ stock solution mentioned above to obtain a pH 7.18 citrate-phosphate buffer.

A-2-2. Preparation of pH 9.0 Carbonate-Bicarbonate Buffer

Water was quantitatively added to 0.11 g of anhydrous sodium carbonate and 0.756 g of sodium bicarbonate to 100 mL and mixed to obtain a pH 9.0 carbonate-bicarbonate buffer.

B. Analytical Method

High Performance Liquid Chromatography (HPLC)

Flavonoid aglycones in the sample were analyzed with high performance liquid chromatography according to the following conditions.

Type of chromatography column: Hypersil Gold aQ 3 um, 4.0×150 mm or equivalent

Detecting wave length: 254 nm

Flow rate of pump: 1.0 mL/minutes

Analysis time per sample: 55 minutes

Column temperature: 35° C.

Total injection volume: 20 μL

Preparation of mobile phases: Mobile phase A=0.1% phosphoric acid aqueous solution; Mobile phase B=Chromatographic grade acetonitrile

TABLE 1

| Time (minutes) | Mobile phase A | Mobile phase B |
|---|---|---|
| 0 | 85 | 15 |
| 30 | 70 | 30 |
| 45 | 50 | 50 |
| 50 | 10 | 90 |
| 51 | 85 | 15 |
| 55 | 85 | 15 |

C. Experimental Methods and Results

Example 1

Effect of Immersion Time on the Ingredients of Flowers of *Chrysanthemum morifolium*

1 g of the dried crumble of flowers of *Chrysanthemum morifolium* mentioned above was added to 20 mL of RO water and placed at room temperature for 0, 1, 5 or 17 hours to form an immersion sample.

Next, 20 mL of 95% ethanol was added to the immersion sample mentioned above and shaken for 30 minutes to form an extract solution.

After that, the extract solution mentioned above was subjected to a solid-liquid separation procedure, and the obtained supernatant was subjected to high performance liquid chromatography to determine the chemical composition changes of extract solutions with different immersion time, wherein two flavonoid aglycones, apigenin and luteolin, were selected as indictor ingredients of *Chrysanthemum morifolium* extract.

The results are shown in FIG. 1. According to FIG. 1, it is known that the content of luteolin and apigenin in the extract solutions increases with the immersion time for the flowers of *Chrysanthemum morifolium*.

Example 2

Effect of Immersion Time on the Extraction Amount of Flavonoid Aglycones from Flowers of *Chrysanthemum morifolium*

In order to investigate the effect of immersion time on the extraction amount of the two flavonoid aglycone indicator ingredients, apigenin and luteolin, of the flowers of *Chrysanthemum morifolium*, the following experiments and analyses were performed.

1 g of the dried crumble of flowers of *Chrysanthemum morifolium* mentioned above was added to 20 mL of RO water and placed at room temperature for 0, 5, 24, 48 or 72 hours to form an immersion sample.

1 mL of the immersion sample mentioned above was taken and centrifuged at 10,000 rpm for 10 minutes, and the obtained supernatant was used as a sample of the immersion solution.

On the other hand, 20 mL of 95% ethanol was added to the rest of the immersion sample and shaken for 30 minutes to form an extract solution.

1 mL of the extract solution mentioned above was taken and centrifuged at 10,000 rpm for 10 minutes to perform a solid-liquid separation procedure, and the obtained supernatant was used as a sample of the extract solution.

The sample of the immersion solution and the sample of the extract solution mentioned above were subjected to high performance liquid chromatography to determine the contents of apigenin and luteolin thereof. The results are shown in Table 2 and FIG. 2.

TABLE 2

The extraction amount per unit herb material (extraction rate) of apigenin and luteolin in the immersion solutions and the extract solutions of the flowers of *Chrysanthemum morifolium* obtained under different immersion time (at room temperature)

| Immersion time (Hours) | Apigenin (mg/g herb material) | | Luteolin (mg/g herb material) | | Apigenin + Luteolin (mg/g herb material) | Apigenin + Luteolin (mg/g herb material) |
|---|---|---|---|---|---|---|
| | Immersion solution | Extract solution | Immersion solution | Extract solution | Immersion solution | Extract solution |
| 0 | 0.85 | 0.51 | 0.19 | 0.20 | 1.04 | 0.71 |
| 1 | 0.92 | 1.17 | 0.20 | 0.35 | 1.12 | 1.52 |
| 5 | 0.85 | 3.55 | 0.28 | 0.92 | 1.13 | 4.47 |

TABLE 2-continued

The extraction amount per unit herb material (extraction rate) of apigenin and luteolin in the immersion solutions and the extract solutions of the flowers of Chrysanthemum morifolium obtained under different immersion time (at room temperature)

| Immersion time (Hours) | Apigenin (mg/g herb material) | | Luteolin (mg/g herb material) | | Apigenin + Luteolin (mg/g herb material) | Apigenin + Luteolin (mg/g herb material) |
|---|---|---|---|---|---|---|
| | Immersion solution | Extract solution | Immersion solution | Extract solution | Immersion solution | Extract solution |
| 24 | 0.31 | 9.43 | 0.16 | 2.72 | 0.47 | 12.15 |
| 48 | 0.24 | 13.05 | 0.14 | 3.35 | 0.38 | 16.4 |
| 72 | 0.00 | 12.57 | 0.08 | 3.09 | 0.08 | 15.66 |

Figure 2:
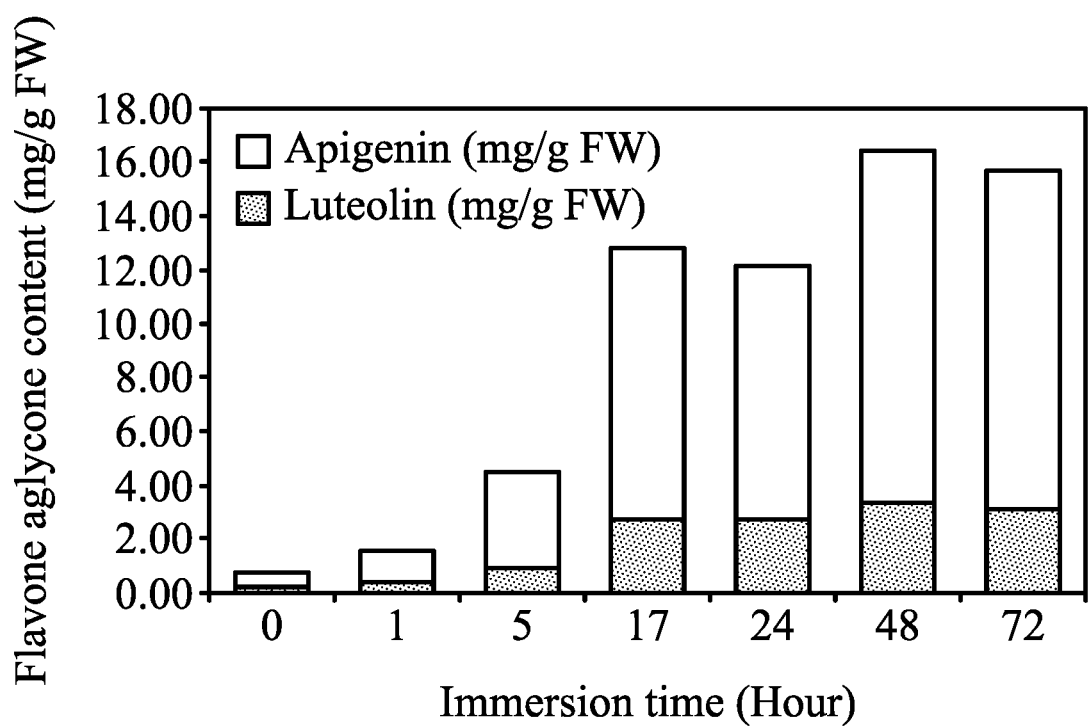
FIG. 2 shows the extraction amounts per unit herb material (extraction rates) of apigenin and luteolin in the immersion solutions and the extract solutions of the flowers of *Chrysanthemum morifolium* obtained under different immersion time (at room temperature)

The results of Table 2 and FIG. 2 show that the extraction amounts of apigenin and luteolin in the immersion solutions decreased with the increase of the immersion time for the flowers of Chrysanthemum morifolium, and in contrast to this, the extraction amounts per unit herb material (extraction rates) of apigenin and luteolin in the extract solutions increase with the increase of the immersion time for the flowers of Chrysanthemum morifolium.

The extract solution obtained by immersing the flowers of Chrysanthemum morifolium at room temperature for 48 hours showed the highest extraction amounts per unit herb material of apigenin and luteolin. Compared to the unimmersed (immersed for 0 hours) extract solution for the flowers of Chrysanthemum morifolium, which only can extract 0.71 mg of apigenin and luteolin per gram of the flowers of Chrysanthemum morifolium, the extract solution obtained by immersing the flowers of Chrysanthemum morifolium at room temperature for 48 hours can extract 16.4 mg of apigenin and luteolin per gram of the flowers of Chrysanthemum morifolium, and the extraction amount thereof is greatly increased to 2300%.

As for the reason why the extraction amounts of apigenin and luteolin in the immersion solution decreases with the increase of immersion time, it is speculated that the precipitation occurs due to poor water solubility of flavonoid aglycones derived from glycoside flavonoid hydrolysis in the immersion solution, and thus after addition of the same amount of 95% ethanol into the immersion solution to form the foregoing extraction solution, the flavonoid aglycones is redissolved in the solution, and the high extraction amount of the flavonoid aglycones is exhibited.

Example 3

Effects of High Temperature and High Pressure Pretreatment on the Extraction Amount of Flavonoid Aglycones in Flowers of Chrysanthemum morifolium 1 g of the dried crumble of flowers of Chrysanthemum morifolium mentioned above was placed in an autoclave and sterilized at 120° C. for 20 minutes. Next, the high temperature and high pressure treated crumble was cooled to room temperature.

After that, the high temperature and high pressure treated crumble was added to 20 mL of RO water and placed at room temperature for 24 hours to form an immersion sample.

Next, 20 mL of 95% ethanol was added to the immersion sample mentioned above and shaken for 30 minutes to form an extract solution.

After that, the extract solution was subjected to a solid-liquid separation procedure, and the obtained supernatant was subjected to high performance liquid chromatography to determine the extraction amounts of apigenin and luteolin in the extraction solution of the high temperature and high pressure treated flowers of Chrysanthemum morifolium.

The results show that the high temperature and high pressure treated sample only can be extracted 0.72 mg of apigenin and luteolin per gram of Chrysanthemum morifolium while the sample without high temperature and high pressure can be extracted up to 12.15 mg of apigenin and luteolin, and there are obvious differences.

This can demonstrate that the increase in the content of apigenin and luteolin during the immersion process is not caused by the natural degradation of the compound itself since according to the foregoing results, even high temperature and high pressure treatment cannot hydrolyze the glycosidic bond.

In contrast, merely by the immersion procedure belonging to mild treatments which is adopted in the present disclosure, through high performance liquid chromatography, it can be observed (referring to FIG. 1) that some ingredients decrease with the increase of immersion time while some ingredients increase with the increase of the immersion time. Therefore, it is speculated that the immersion procedure may activate the activity of the hydrolytic enzymes against the Chrysanthemum morifolium endogenous glycosidic bonds, thereby increasing the extraction amounts of apigenin and luteolin.

Example 4

Effects of Immersion Temperature and pH Value on the Extraction Amount of Flavonoid Aglycones in Flowers of Chrysanthemum morifolium In order to investigate the optimum temperature and pH value for immersion, 1 g of the dried crumble of flowers of Chrysanthemum morifolium mentioned above was added to 20 mL of RO water or buffer aqueous solutions with different pH values (pH 2.7, pH 5.0, pH 7.18 and pH 9.2) and placed at a temperature of 4° C., 25° C. or 50° C. for 24 hours to form an immersion sample.

Next, 20 mL of 95% ethanol was added to the immersion sample mentioned above and shaken for 30 minutes to form an extract solution.

After that, the extract solution mentioned above was subjected to a solid-liquid separation procedure, and the obtained supernatant was subjected to a content analysis through high performance liquid chromatography.

Figure 3A:
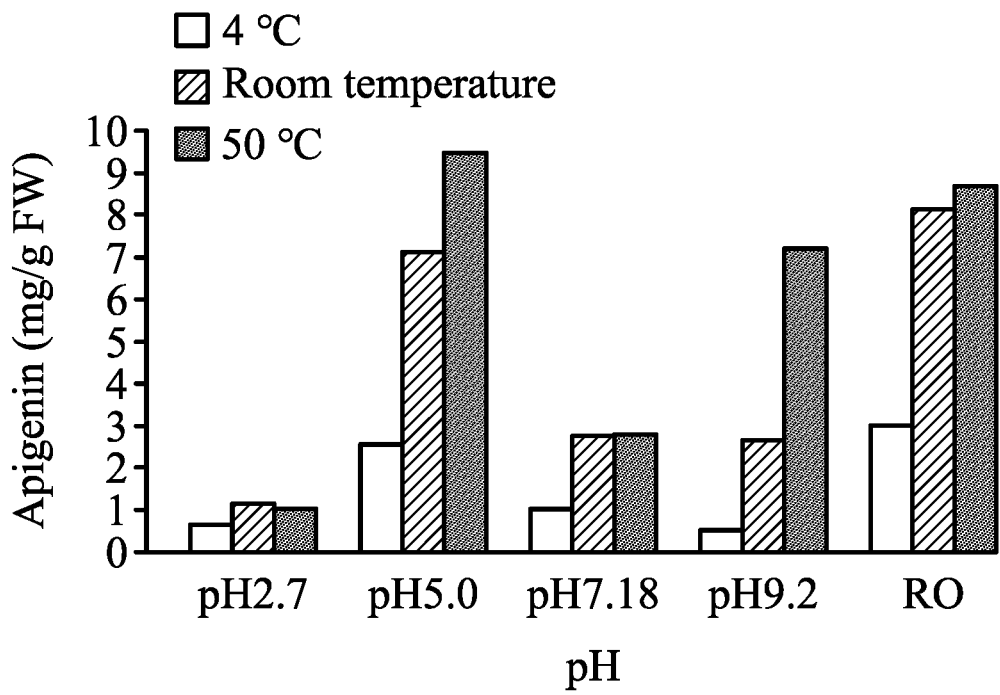
FIG. 3A shows the extraction amount per unit herb material (extraction rate) of apigenin in the extract solutions of the flowers of *Chrysanthemum morifolium* obtained under different pH values and different immersion temperature. FW: Weight of flowers of *Chrysanthemum morifolium*.
Figure 3B:
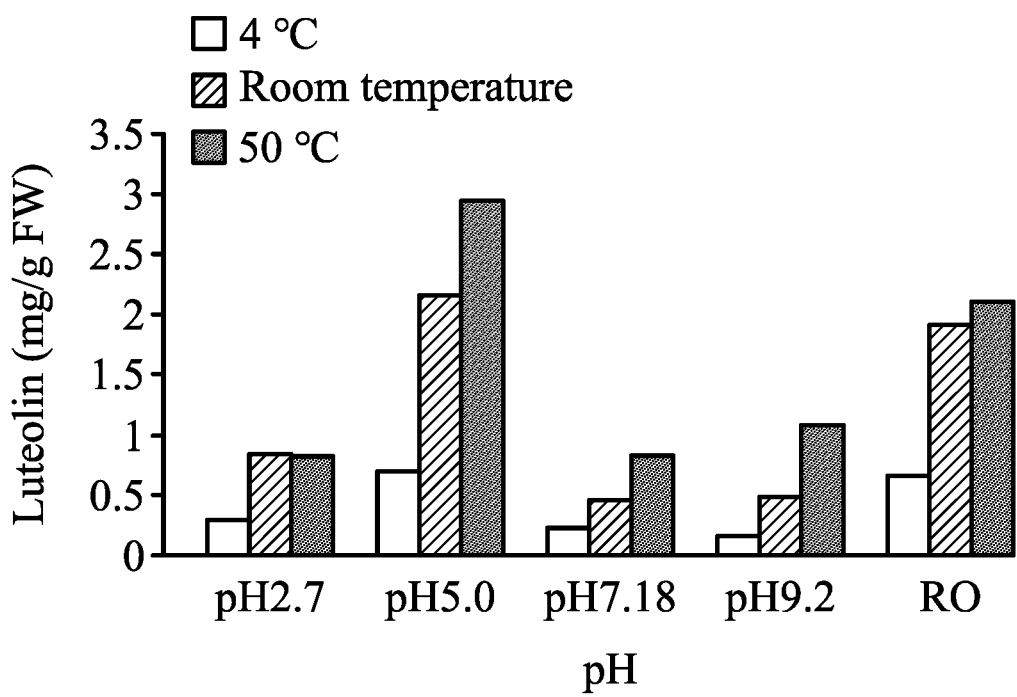
FIG. 3B shows the extraction amount per unit herb material (extraction rate) of luteolin in the extract solutions of the flowers of *Chrysanthemum morifolium* obtained under different pH values and different immersion temperature. FW: Weight of flowers of *Chrysanthemum morifolium*.

The results are shown in FIG. 3. Based on FIG. 3, it is known that no matter whether the flowers of Chrysanthemum morifolium were immersed in RO water or buffered aqueous solution with pH 2.7 to 9.2, when the immersion temperature increases from 4° C. to 50° C., the extraction amounts of apigenin and luteolin increase with the increase of immersion temperature. When the pH value of the buffer aqueous solution used to immerse the flowers of *Chrysanthemum morifolium* increases from 2.7 to 5.0, the extraction amounts of apigenin and luteolin increases with the increase of pH value, however, the extraction amounts of apigenin and luteolin under the pH value of the buffer aqueous solution being 7.18 and 9.2 is lower than the extraction amounts of apigenin and luteolin under the pH value of the buffer aqueous solution being 5.0.

The extraction amounts of apigenin and luteolin of only immersing the flowers of *Chrysanthemum morifolium* in RO water was slightly lower than the extraction amounts of apigenin and luteolin of immersing the flowers of *Chrysanthemum morifolium* in a pH 5.0 buffer aqueous solution. The pH value of RO water after immersing the flowers of *Chrysanthemum morifolium* was determined to be 4.5, and that was consistent with the observed result in which the extraction amounts of apigenin and luteolin increased with the increase of pH value under the pH value of the buffer aqueous solution used to immerse the flowers of *Chrysanthemum morifolium* increasing from 2.7 to 5.0. Although the extraction amount of apigenin and luteolin after immersion in RO water was slightly lower than the extraction amounts of apigenin and luteolin after immersion in a pH 5.0 buffer aqueous solution, direct immersion in RO water is a simpler, more convenient cost-saving operation.

Example 5

Immersion Extraction with 50% Ethanol Aqueous Solution 1 g of the dried crumble of flowers of *Chrysanthemum morifolium* mentioned above was added to 40 mL of 50% ethanol aqueous solution and uniformly shaken, and then placed at room temperature for 1, 5 or 24 hours to form an immersion sample.

The immersion sample mentioned above was shaken for 30 minutes to form an extract solution.

After that, the extract solution mentioned above was subjected to a solid-liquid separation procedure, and the obtained supernatant was subjected to a content analysis through high performance liquid chromatography. The results are shown in Table 3.

TABLE 3

Extraction amount of apigenin and luteolin after immersion in 50% ethanol aqueous solution

| Immersion time (Hours) | Apigenin (mg/g FW) Extraction solution | Luteolin (mg/g FW) Extraction solution | Apigenin + Luteolin (mg/g FW) Extraction solution |
|---|---|---|---|
| 1 | 0.42 | 0.18 | 0.6 |
| 5 | 0.45 | 0.21 | 0.66 |
| 24 | 0.52 | 0.31 | 0.83 |

FW: Weight of flowers of *Chrysanthemum morifolium*

According to Table 3, it is known that the immersion procedure performed with 50% ethanol aqueous solution cannot increase the extraction amounts of apigenin and luteolin.

Example 6

Effect of Immersion Time on the Ingredients of Stems and Leaves of *Chrysanthemum morifolium*

For *Chrysanthemum morifolium*, after the flowers are harvested, the stems and leaves are generally discarded as agricultural waste. In this study, it is found that the stems and leaves of *Chrysanthemum morifolium* also contain a large amount of flavonoid glycosides. Although the glycosyl derivatives of flavonoid aglycones contained in the stems and leaves of *Chrysanthemum morifolium* are different from those of flowers, they are still mainly derived from apigenin and luteolin. Therefore, if the flowers of *Chrysanthemum morifolium* through the immersion process can increase the extraction amount of flavonoid aglycone by activating the endogenous glycoside hydrolase of *Chrysanthemum morifolium*, stems and leaves belonging to different parts of the same plant may have the same effect. Moreover, if the extraction amount of apigenin and luteolin from stems and leaves can be increased by an immersion manner, the stems and leaves of *Chrysanthemum morifolium*, which are agricultural wastes, can be given a high economic value, and the effect of waste recycling can be achieved.

1 g of the dried crumble of stems and leaves of *Chrysanthemum morifolium* mentioned above was added to 20 mL of RO water and placed at room temperature for 0, 1, 5, 24, 48 or 72 hours to form an immersion sample.

20 mL of 95% ethanol was added to the immersion sample mentioned above and shaken for 30 minutes to form an extract solution.

After that, the extract solution was subjected to a solid-liquid separation procedure, and the obtained supernatant was subjected to high performance liquid chromatography to determine the chemical composition changes of extract solutions with different immersion time. The results are shown in FIG. 4.

Figure 4:
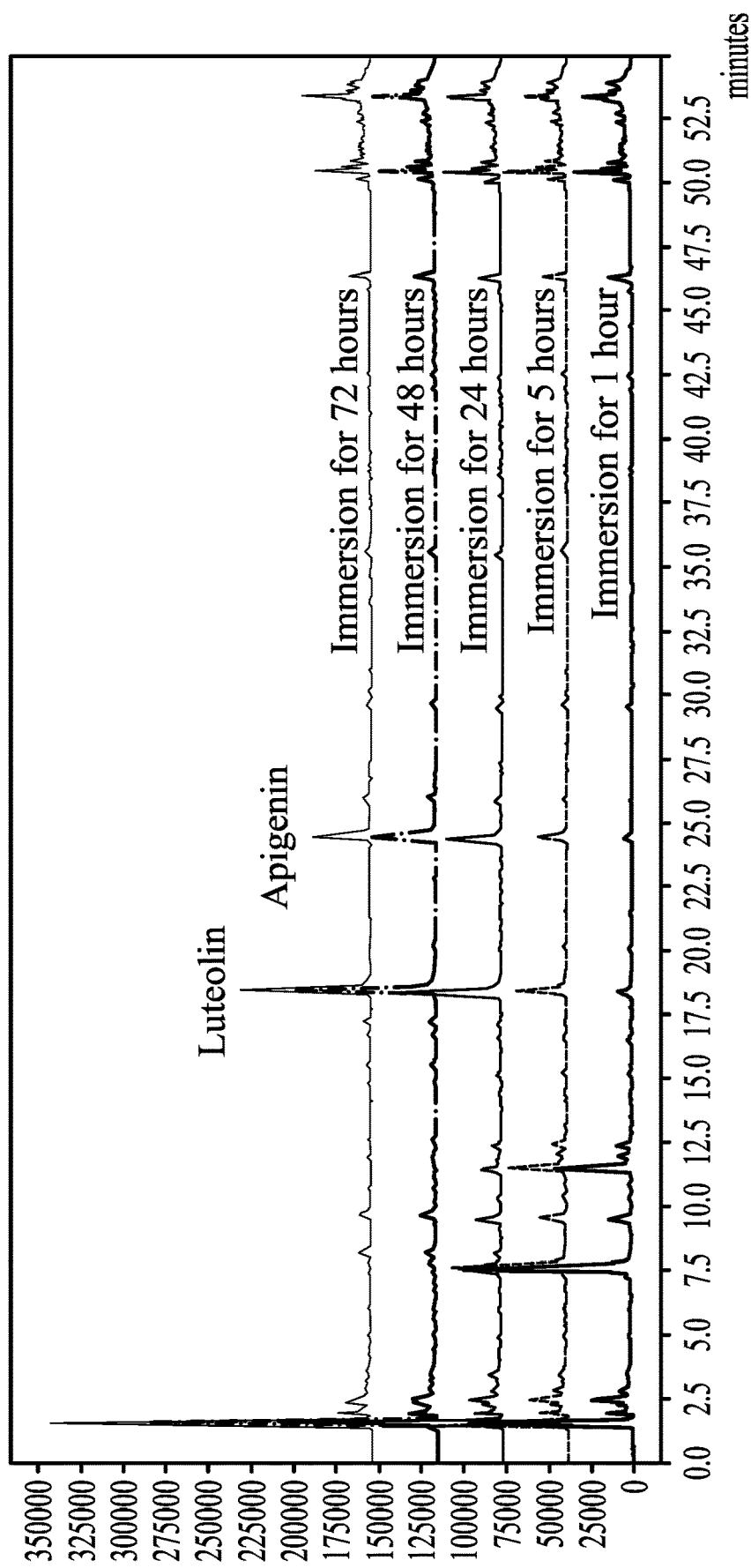
FIG. 4 shows the high performance liquid chromatograms of the extract solutions of the stems and leaves of *Chrysanthemum morifolium* obtained under different immersion time (at room temperature)
Figure 5:
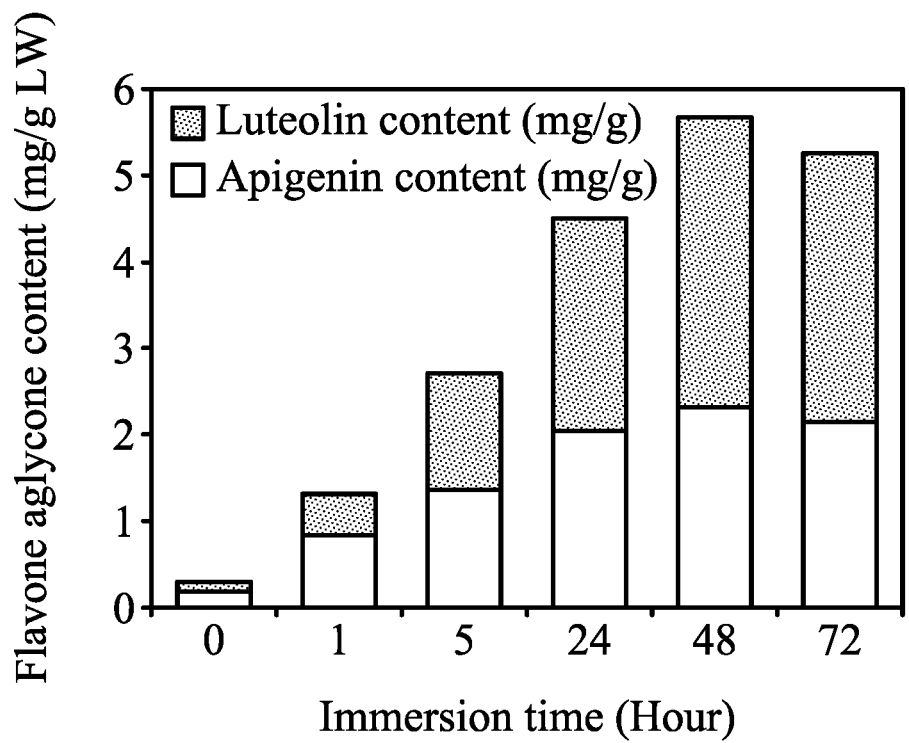
FIG. 5 shows the extraction amounts per unit herb material (extraction rate) of apigenin and luteolin in the extract solutions of the stems and leaves of *Chrysanthemum morifolium* obtained under different immersion time (at room temperature). LW: Weight of stems and leaves of *Chrysanthemum morifolium*.

The extraction amounts of apigenin and luteolin were respectively calculated based on the high performance liquid chromatograms show in FIG. 4. The results are shown in FIG. 5 and Table 4.

TABLE 4

The extraction amount per unit herb material (extraction rate) of apigenin and luteolin in the immersion solution and the extract solution of stems and leaves of *Chrysanthemum morifolium* obtained under different immersion time (at room temperature)

| Immersion time (Hours) | Apigenin (mg/g LW) Extraction solution | Luteolin (mg/g LW) Extraction solution | Apigenin + Luteolin (mg/g LW) Extraction solution |
|---|---|---|---|
| 0 | 0.19 | 0.11 | 0.3 |
| 1 | 0.85 | 0.47 | 1.32 |
| 5 | 1.38 | 1.32 | 2.7 |
| 24 | 2.05 | 2.48 | 4.53 |
| 48 | 2.34 | 3.35 | 5.69 |
| 72 | 2.16 | 3.12 | 5.28 |

LW: Weight of stems and leaves of *Chrysanthemum morifolium*

FIG. 5 and Table 4 show that after the stems and leaves of *Chrysanthemum morifolium* were immersed for a fixed period of time at room temperature, the extraction amounts of apigenin and luteolin increase with the increase of immersion time, wherein compared to the unimmersed sample which only can be extracted 0.3 mg of apigenin and luteolin per gram of stems and leaves of *Chrysanthemum morifolium*, the stems and leaves of *Chrysanthemum morifolium* after being immersed for 48 hours, can be extracted 5.69 mg of total amount of apigenin and luteolin per gram, and the total extraction amount increases to 1890%, and the total extraction rate is significantly increased.

Example 7

Antioxidant Activity Analysis of Extracts from Stems and Leaves of *Chrysanthemum morifolium*

1. Preparation of Extract of Stems and Leaves of *Chrysanthemum morifolium*

CML-A: 10 g of the dried crumble of stems and leaves of *Chrysanthemum morifolium* mentioned above was added to 200 mL water and immersed at room temperature for 24 hours to form an immersion sample. Next, the immersion sample was centrifuged and the water layer was discarded. The residue was added to 200 mL 95% ethanol and shaken for 30 minutes, and then a solid-liquid separation was performed and the obtained extract solution was concentrated and dried under reduced pressure.

CML-B: 10 g of the dried crumble of stems and leaves of *Chrysanthemum morifolium* mentioned above was added to 200 mL 50% ethanol aqueous solution (95% ethanol: water=1:1 v/v) and shaken for 30 minutes, and then a solid-liquid separation was performed and the obtained extract solution was concentrated and dried under reduced pressure.

CML-C: 10 g of the dried crumble of stems and leaves of *Chrysanthemum morifolium* mentioned above was added to 200 mL water and boiled and refluxed for 1 hour, and then a solid-liquid separation was performed and the obtained extract solution was concentrated and dried under reduced pressure.

2. Antioxidant Activity Analysis

The antioxidant activity analysis platform constructed by monocyte/macrophage-like (RAW264.7) cells was used to evaluate the effect of the extract of the stems and leaves of *Chrysanthemum morifolium* prepared above on RAW264.7 cells and the antioxidant activity of the extract of the stems and leaves of *Chrysanthemum morifolium* prepared above.

The detailed experimental steps are as follows: the cells were divided into a negative control group, a positive control group and 3 experimental groups. The negative control group was the cells without any treatment, the positive control group was the cells treated with 10 μM and 100 μM apigenin, and the three experimental groups were cells respectively treated with CML-A (12.5 to 100 μg/mL), CML-B (12.5 to 100 μg/mL) and CML-C (12.5 to 100 μg/mL).

After RAW264.7 cells were cultured in a 96-well plate overnight, 100 ng/mL LPS was added to the positive control group and the experimental groups to induce cell inflammation. After the cell culturing were continued for 24 hours, the cell culture supernatant was collected and temporarily stored in a −20° C. refrigerator for subsequent experiments.

In the cell viability assay, 50 μL of MTT (5 mg/mL) was added to the cells in each well and reacted at 37° C. for 20 minutes. After that, 150 μL of DMSO solvent was added to each well. The culture plate was shaken on an orbital shaker for 5 minutes to completely dissolve the MTT crystals and the absorbance at 590 nm was read.

Cell viability was calculated based on the following formula:

Cell viability (%)=(Fluorescence value of test substance/Fluorescence value of negative control group)×100

Figure 6A:
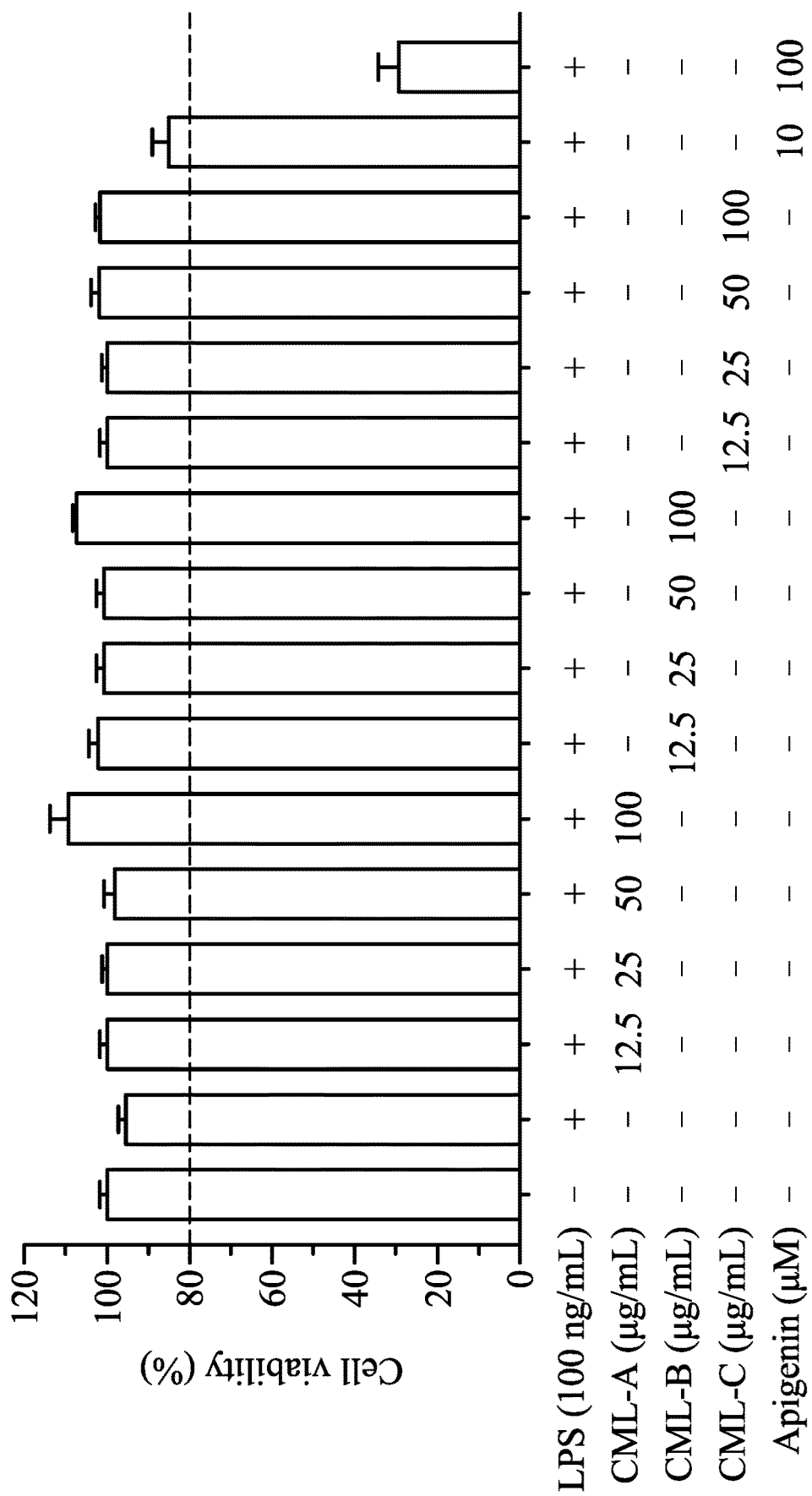
FIG. 6A shows cell viability of RAW264.7 cells treated with the extract solutions of the stems and leaves of *Chrysanthemum morifolium*. Apigenin is the positive control group. Data represent mean±standard deviation (n=3)

The results are shown in FIG. 6A. According to FIG. 6A, it is known that the extract of the stems and leaves *Chrysanthemum morifolium* (CML-A, CML-B and CML-C) do not affect the cell viability of RAW264.7 cells.

In the cellular nitric oxide ($NO^{2-}$) assay, $NO^{2-}$ production was determined by measuring the nitrite ($NO_2$) amount of in the cell culture supernatant according to the procedure of the manufacturer, Promega, for Griess kit. The absorbance at 540 nm was read, and $NO^{2-}$ production was calculated. The results are shown in FIG. 6B.

Figure 6B:
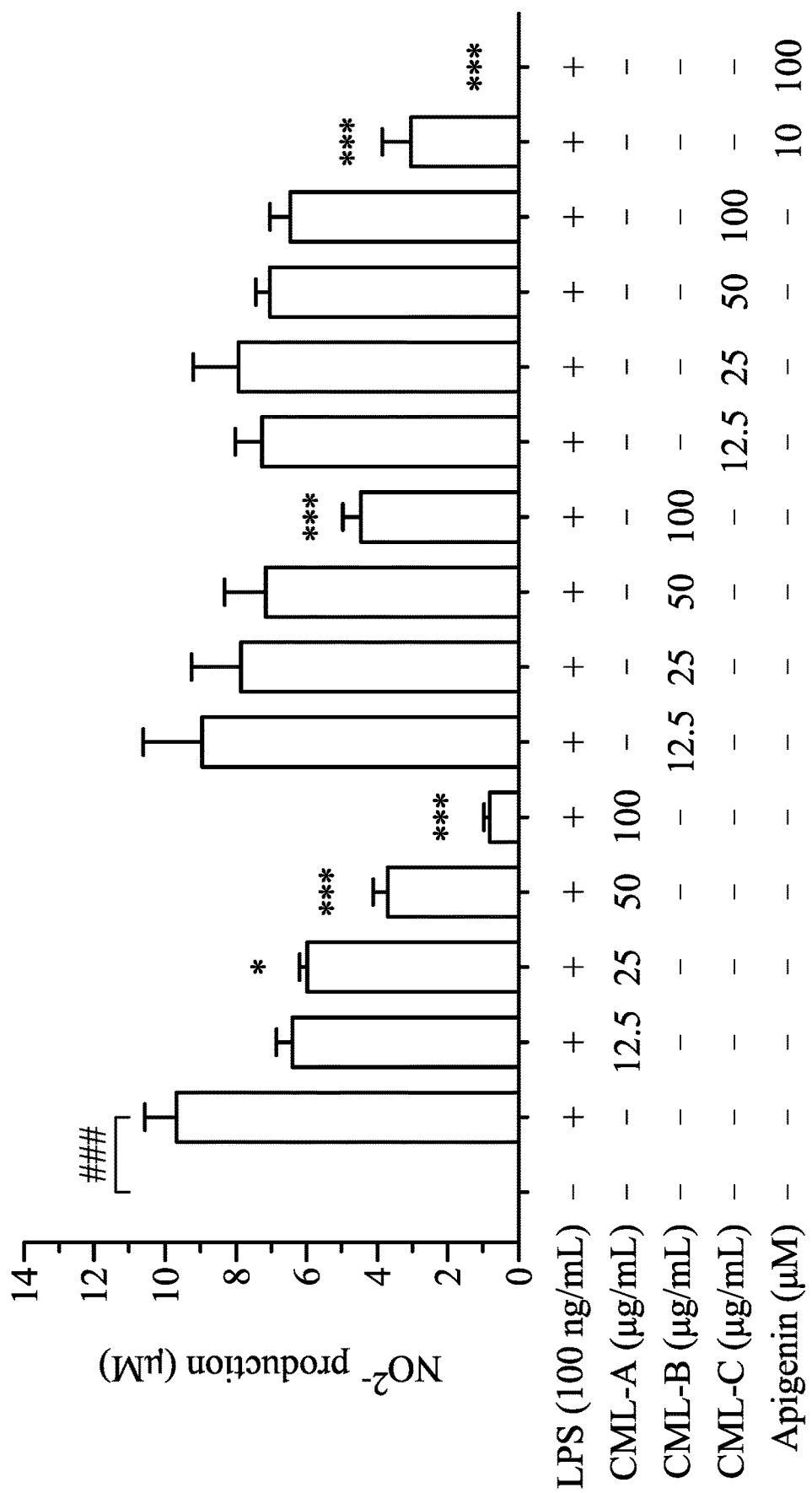
FIG. 6B shows $NO^{2-}$ inflammatory factor production of RAW264.7 cells treated with the extract solutions of the stems and leaves of *Chrysanthemum morifolium*. Apigenin is the positive control group. ###:p<0.001, compared to the negative control group. *:p<0.05, ***:p<0.001, compared to the group only treated with LPS. Data represent mean±standard deviation (n=3); The statistical method is one-way analysis of variance (one-way ANOVA) and Dunnett's multiple comparison.

FIG. 6B shows that CML-A 25 μg/mL, 50 μg/mL and 100 g/mL, and CML-B 100 μg/mL significantly reduce the production of $NO^{2-}$ inflammatory factor.

In the Interleukin-6 (IL-6) assay, Sandwich Enzyme-linked immunosorbent assay (ELISA) was used for the test. The detailed experimental steps are as follows:

Antibodies were immobilized on a 96-well plate and placed at 4° C. overnight. On the next day, the antibodies which are not immobilized and impurities were washed away, and the cell supernatant (specimen) was added to the plate to make the antigens in the specimens bind to the immobilized antibodies. After reacting at room temperature for 2 hours, the excess specimens were washed away, and then antigen-specific antibodies with HRP were added to make the antigens in the specimen bind thereto. After 1 hour of reaction at room temperature, the unbound antibodies were washed away, and the enzyme substrates were added for coloration. The content of the antigen to be tested was calculated by the absorbance at 450 nm to calculate the concentration of IL-6. The results are shown in FIG. 6C.

Figure 6C:
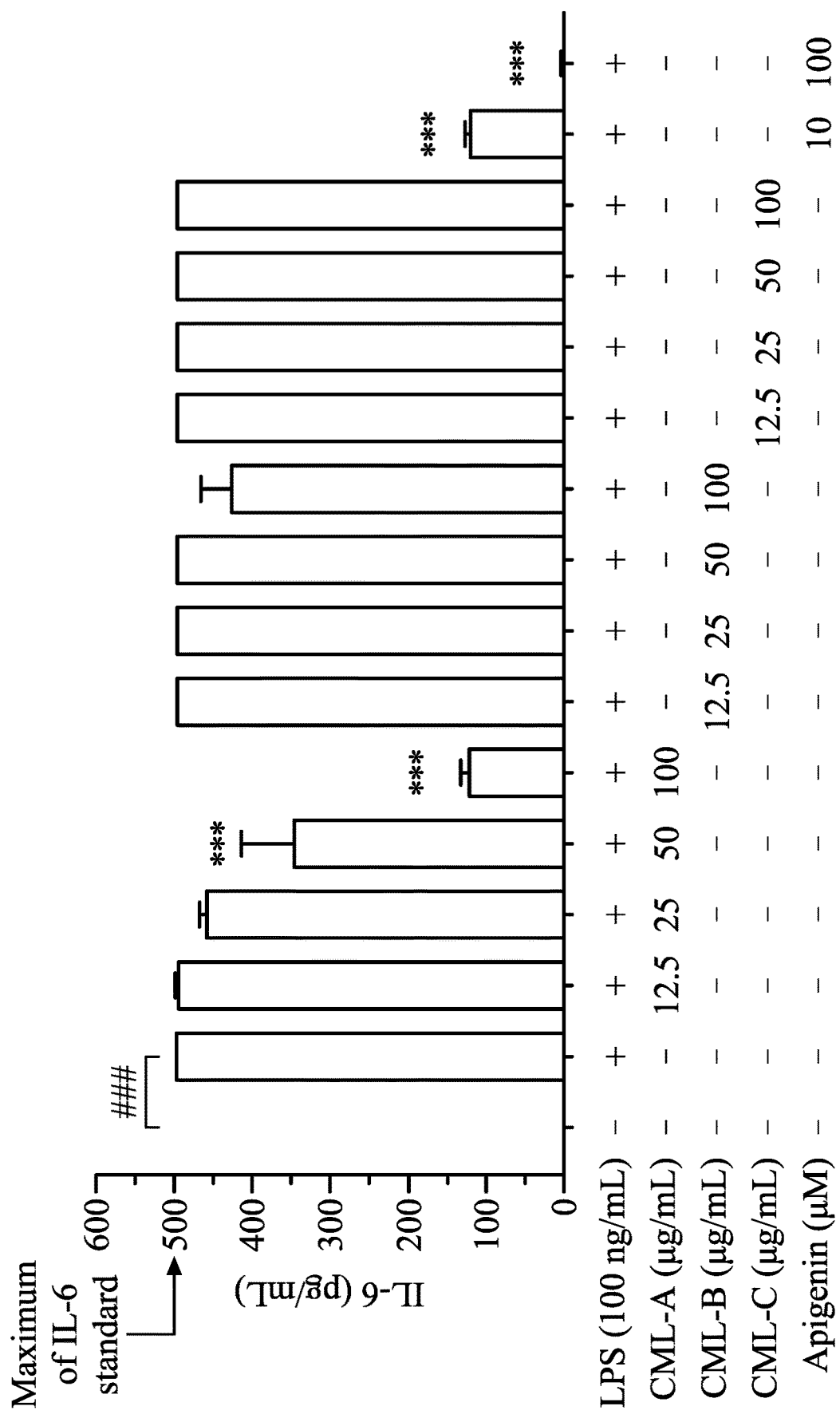
FIG. 6C shows IL-6 expression level of RAW264.7 cells treated with the extract solutions of the stems and leaves of *Chrysanthemum morifolium*. Apigenin is the positive control group. ###:p<0.001, compared to the negative control group. ***: p<0.001, compared to the group only treated with LPS. Data represent mean±standard deviation (n=3); The statistical method is one-way analysis of variance (one-way ANOVA) and Dunnett's multiple comparison.

FIG. 6C shows that CML-A 50 μg/mL and 100 μg/mL can significantly reduce the expression level of IL-6 inflammatory factor.

According to the foregoing results, the extract obtained by the extraction method of the present disclosure has an excellent anti-inflammatory effect.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for extracting flavone aglycones in *Chrysanthemum morifolium*, comprising:
   (a) immersing a *Chrysanthemum morifolium* raw material in water or an aqueous solution to perform an immersion procedure for 3.5 hours or more to obtain an immersion sample,
   wherein
      the *Chrysanthemum morifolium* raw material comprises at least one of the following parts of *Chrysanthemum morifolium*:
      a whole plant, a root, a stem, a leaf, and a flower,
      a weight ratio of the *Chrysanthemum morifolium* raw material to the water or aqueous solution is 1:10-35,
      the immersion procedure is performed at 20 to 70° C.,
      the water or aqueous solution has a pH value of 3.0 to 9.5, and
      the immersion sample comprises an immersed *Chrysanthemum morifolium* raw material and an immersion solution; and
   (b) adding an extraction solvent to the immersion sample to perform an extraction procedure for 5-60 minutes to obtain an extract solution,
   wherein
      a weight ratio of the *Chrysanthemum morifolium* raw material to the extraction solvent is 1:10-35,
      the extraction solvent comprises methanol, ethanol or ethyl acetate, the extraction procedure is performed at 15 to 50° C., and the extract solution contains flavone aglycones.

2. The method for extracting flavone aglycones in *Chrysanthemum morifolium* as claimed in claim 1, wherein the *Chrysanthemum morifolium* raw material is subjected to a pretreatment.

3. The method for extracting flavone aglycones in *Chrysanthemum morifolium* as claimed in claim 2, wherein the pretreatment comprises at least one of the following:
   a drying treatment; and
   a pulverizing treatment.

4. The method for extracting flavone aglycones in *Chrysanthemum morifolium* as claimed in claim 1, further comprising, between step (a) and step (b), removing the immersion solution in the immersion sample.

5. The method for extracting flavone aglycones in *Chrysanthemum morifolium* as claimed in claim 1, wherein the immersion procedure is performed for 5 to 96 hours.

6. The method for extracting flavone aglycones in *Chrysanthemum morifolium* as claimed in claim 1, wherein the weight ratio of the *Chrysanthemum morifolium* raw material to the water or aqueous solution is 1:15-30.

7. The method for extracting flavone aglycones in *Chrysanthemum morifolium* as claimed in claim 1, wherein the immersion procedure is performed at room temperature to 70° C.

8. The method for extracting flavone aglycones in *Chrysanthemum morifolium* as claimed in claim 1, wherein the water or aqueous solution has a pH value of 4.0 to 9.5.

9. The method for extracting flavone aglycones in *Chrysanthemum morifolium* as claimed in claim 1, wherein the extraction procedure is performed for 10 to 40 minutes.

10. The method for extracting flavone aglycones in *Chrysanthemum morifolium* as claimed in claim 1, wherein the weight ratio of the *Chrysanthemum morifolium* raw material to the extraction solvent is 1:15-30.

11. The method for extracting flavone aglycones in *Chrysanthemum morifolium* as claimed in claim 1, wherein the extraction procedure is performed at room temperature to 40° C.

12. The method for extracting flavone aglycones in *Chrysanthemum morifolium* as claimed in claim 1, wherein the *Chrysanthemum morifolium* raw material is a flower of the *Chrysanthemum morifolium*.

13. The method for extracting flavone aglycones in *Chrysanthemum morifolium* as claimed in claim 12, wherein the immersion procedure is performed for 5 to 72 hours, the weight ratio of the *Chrysanthemum morifolium* raw material to the water or aqueous solution is 1:15-20, and the immersion procedure is performed at room temperature to 50° C., the water or aqueous solution has a pH value of 5.0 to 9.2, and the extraction solvent is ethanol, and wherein an extraction rate of flavone aglycones of the *Chrysanthemum morifolium* raw material in the method for extracting flavone aglycones in *Chrysanthemum morifolium* is 2-30 mg flavone aglycones/g *Chrysanthemum morifolium* raw material.

14. The method for extracting flavone aglycones in *Chrysanthemum morifolium* as claimed in claim 1, wherein the *Chrysanthemum morifolium* raw material is a stem and a leaf of the *Chrysanthemum morifolium*.

15. The method for extracting flavone aglycones in *Chrysanthemum morifolium* as claimed in claim 14, wherein the immersion procedure is performed for 5 to 72 hours, the weight ratio of the *Chrysanthemum morifolium* raw material to the water or aqueous solution is 1:15-20, and the immersion procedure is performed at room temperature to 50° C., the water or aqueous solution has a pH value of 5.0 to 9.2, and the extraction solvent is ethanol, and wherein an extraction rate of flavone aglycones of the *Chrysanthemum morifolium* raw material in the method for extracting flavone aglycones in *Chrysanthemum morifolium* is 2-25 mg flavone aglycones/g *Chrysanthemum morifolium* raw material.

16. The method for extracting flavone aglycones in *Chrysanthemum morifolium* as claimed in claim 1, further comprising, performing step (c) after step (b), performing a solid-liquid separation procedure on the extract solution to obtain a supernatant, wherein the supernatant contains the flavone aglycones.

17. The method for extracting flavone aglycones in *Chrysanthemum morifolium* as claimed in claim 16, further comprising, after step (c), separating and purifying the flavone aglycones from the supernatant.

18. The method for extracting flavone aglycones in *Chrysanthemum morifolium* as claimed in claim 1, wherein the flavone aglycones comprise luteolin, apigenin or a combination thereof.

\* \* \* \* \*